United States Patent
Lemistre et al.

(10) Patent No.: US 7,460,963 B2
(45) Date of Patent: Dec. 2, 2008

(54) DEVICE AND METHOD FOR HEALTH MONITORING OF AN AREA OF A STRUCTURAL ELEMENT, AND STRUCTURE ADAPTED FOR HEALTH MONITORING OF AN AREA OF A STRUCTURAL ELEMENT OF SAID STRUCTURE

(75) Inventors: Michel Bernard Lemistre, Livry-Gargan (FR); Dominique Marc Placko, Creteil (FR)

(73) Assignees: Centre National de la Recherche Scientifique (CNRS), Paris (FR); Office National d'etudes et de Recherches Aerospatiales (ONERA), Chatillon (FR); Ecole Normale Superieure de Cachan, Cachan (FR)

( * ) Notice: Subject to any disclaimer, the term of this patent is extended or adjusted under 35 U.S.C. 154(b) by 498 days.

(21) Appl. No.: 10/813,466

(22) Filed: Mar. 30, 2004

(65) Prior Publication Data
US 2005/0228208 A1 Oct. 13, 2005

(51) Int. Cl.
*G01B 5/30* (2006.01)
*G06F 19/00* (2006.01)

(52) U.S. Cl. .......................... 702/38; 702/40; 702/188; 702/189; 324/765

(58) Field of Classification Search ................... 702/38, 702/39, 40, 57, 58, 59, 60, 121, 155, 156, 702/188, 189, 190; 600/9; 324/765, 464
See application file for complete search history.

(56) References Cited

FOREIGN PATENT DOCUMENTS

FR 2847051 5/2004
WO WO-2004/044790 5/2004

OTHER PUBLICATIONS

Lemistre et al. "Simulation of an electromagnetic health monitoring concept for composite materials. Comparison with experimental data", vol. 5047, 2003, pp. 130-139.*
Lemistre, et al., "Electromagnetic localization of defects in carbon epoxy composite materials", SPIE, vol. 3399, 1988, pp. 89-96.
Lemistre, et al., "Electromagnetic Structural Health Monitoring for Composite Materials", Structurel Health Monitoring, The Demands and Challenges, Ed. F.K. Chang, CRC Press, 2001, pp. 1281-1290.

(Continued)

*Primary Examiner*—Eliseo Ramos-Feliciano
*Assistant Examiner*—Phuong Huynh
(74) *Attorney, Agent, or Firm*—Marshall, Gerstein & Borun LLP

(57) ABSTRACT

Device for health monitoring of a structure comprising a dielectric material of permittivity $\epsilon_r$, comprising a source of electromagnetic radiation, generating an electric field in the structure a detector measuring a component of the electric field, calculation means giving the value of $\epsilon_r$ on the basis of the said component.

27 Claims, 9 Drawing Sheets

OTHER PUBLICATIONS

Lemistre et al., "Electromagnetic Health Monitoring System for Composite Material", Matériaux et Techniques, numéro hors série 2002, Ed. SIRPE, Paris, pp. 29-32.

Lemistre, "Le Contrôle non destructif à l'Onera".

Lemistre et al., "Stimulation of an electromagnetic health monitoring concept for composite materials. Comparison with experimental data", Action spécifique AS58 "Contrôle non destructif—Intégration multi-capteurs", compte-rendu de la reunion du 31 mars 2003 au 1$^{er}$ avril 2003.

Lemistre M.; Placko D.; "Evaluation of the Performances of an Electromagnetic SHM System for Composite, Comparison between Numerical Simulation, Experimental Data and Ultrasonic Investigation", SPIE 9th NDE for Health Monitoring, San Diego (USA), Mar. 14, 2004.

M.B. Lemistre and D.L. Balageas: "A Hybrid Electomagnectic Acouso-Ultrasonic Method for SHM of Carbon/Epoxy Structure", Structural Health Monitoring, vol. 2, No. 2, 2003, pp. 153-160.

Lemistre Michel B. et al.: "Stimulation of an Electo-Magnetic Health Monitoring Concept for Composite Materials, Comparison with Experimental Data", proceedings of SPIE, the International society for optical engineering, vol. 5047, 2003, pp. 130-139.

French Preliminary Search Report FR 0403310; report dated Oct. 27, 2004.

International Search Report received in International (PCT) Application PCT/FR2005/000731, issued Mar. 30, 2004.

Written Opinion for Application PCT/FR2005/000731, issued Mar. 30, 2004.

\* cited by examiner

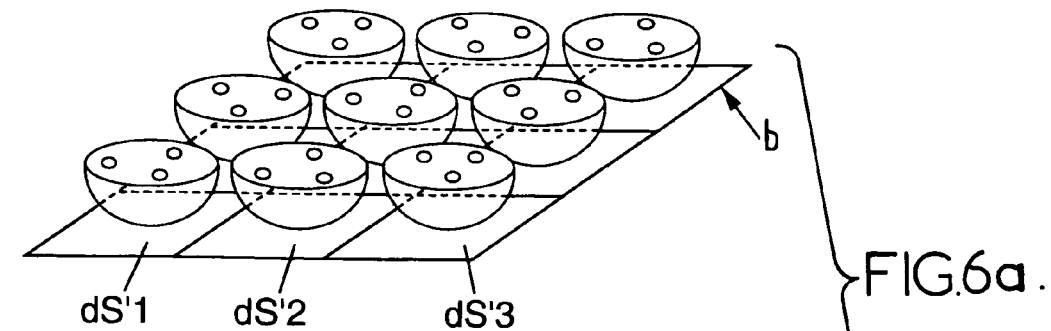
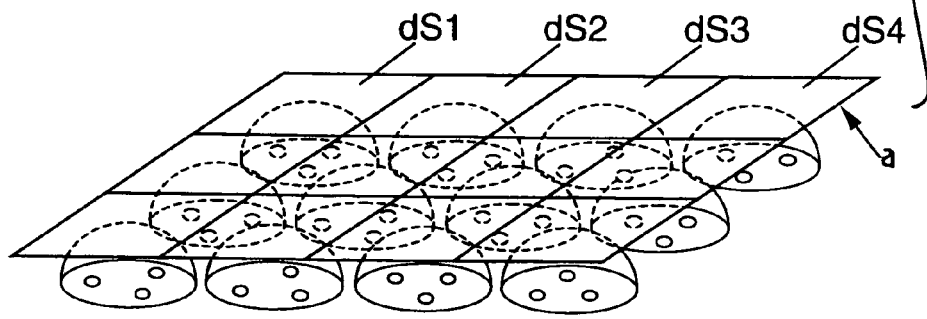
FIG.6a.
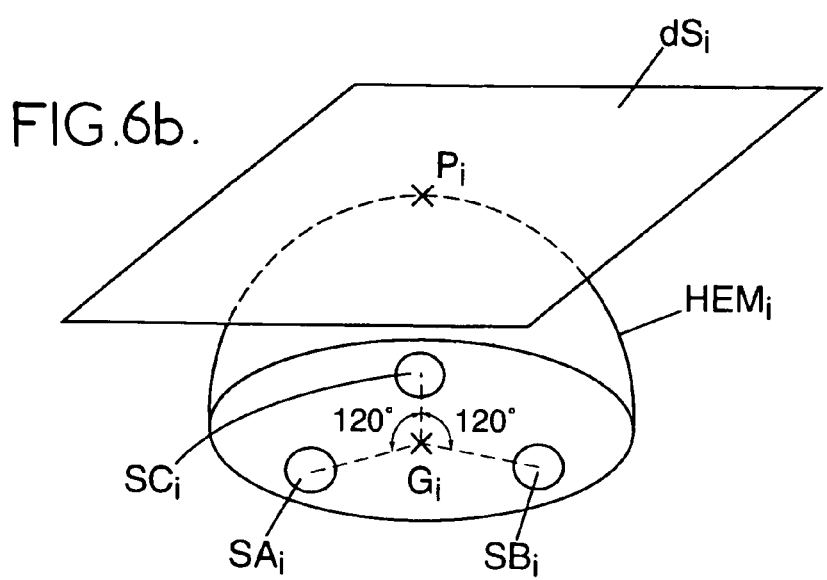
FIG.6b.

DEVICE AND METHOD FOR HEALTH MONITORING OF AN AREA OF A STRUCTURAL ELEMENT, AND STRUCTURE ADAPTED FOR HEALTH MONITORING OF AN AREA OF A STRUCTURAL ELEMENT OF SAID STRUCTURE

FIELD OF THE INVENTION

The present invention relates to devices and methods for health monitoring of an area of a structural element, and to a structure adapted for health monitoring of an area of a structural element of this structure.

TECHNOLOGICAL BACKGROUND

More particularly, the invention concerns a device for health monitoring of an area of a structural element comprising at least one dielectric material of dielectric permittivity $\epsilon_r$, comprising:
(A) means of emission of electromagnetic radiation extending in a direction, the said electromagnetic field generating an electric field in the area, and
(B) detection means suitable for measuring a first measured component of an electric field, along a first direction of detection.

The structural elements in question are typically materials made of resin reinforced with glass fibres or carbon fibres, forming part of the structure, for example of a vehicle such as a motor vehicle, an aircraft, a railway vehicle, or the like, for which the weight constraints are paramount.

Such a device has already been used with success in the past to determine whether such a structural element exhibited a defect, for example of a mechanical or chemical nature, or the like. Such an example of an application is described in "Electromagnetic health monitoring system for composite materials", Lemistre and Balageas, in Matériaux et Techniques, special issue 2002, published by SIRPE, Paris, pg 29-32.

In this article, the electromagnetic field is, for structures comprising carbon fibres, a magnetic field locally equivalent to the magnetic field emitted by a dipole extending along a given direction of the structural element and is emitted by two linear conducting tracks extending in this direction and traversed in opposite senses by an electric current. The electric field is measured orthogonally to this direction in the plane of the structure. The information thus gleaned is useful for determining whether the structure does or does not exhibit a defect.

For structures comprising glass fibres or simply a resin, the exciter field is an electromagnetic field emitted by the tracks extending likewise in this direction.

Such a device makes it possible to qualify the presence or otherwise of a structural defect in the structure under study, but does not make it possible to determine the gravity of the defect. In the presence of a defect, the user of the device will not know what to do: wait or replace the structure (thereby guaranteeing safety to the detriment of cost) even if the defect is not perhaps penalizing per se for the structure in its daily application.

SUMMARY

Thus, according to the invention, a device of the kind in question is essentially characterized in that the said device furthermore comprises calculation means suitable for obtaining a value of the dielectric permittivity $\epsilon_r$ in the said area on the basis of the said first measured component.

By virtue of these arrangements, information pertaining to the structural element is obtained, making it possible to quantify the gravity of the defect exhibited by the structural element, since an intrinsic characteristic of the material is determined.

In practice, this makes it possible to forecast the type of intervention to be undertaken with regard to the structural element, to eliminate the defect, rather than to have to replace the entire structural element through ignorance.

In preferred embodiments of the invention, recourse may possibly be had moreover to one and/or other of the following arrangements:
  the said structural element is an inhomogeneous structural element furthermore comprising an imperfectly conducting material, of electrical conductivity $\sigma$, the means of emission are means of emission of magnetic radiation that are suitable for generating a magnetic field, the said magnetic field being, at the area, equivalent to a magnetic field emitted by a magnetic dipole extending in the said direction, and the calculation means are alternatively or furthermore suitable for obtaining a value of the electrical conductivity $\sigma$ in the said area on the basis of the said first measured component;
  the said detection means are suitable for furthermore measuring a second measured component of the said electric field, along a second direction of detection forming with the said first direction of detection a nonzero angle, and the calculation means are suitable for obtaining a value of the electrical conductivity $\sigma$ and of the electrical permittivity $\epsilon_r$ in the said area on the basis of the said first and the said second measured components;
  a direction chosen from the first and the second direction of detection is the said direction of means of emission;
  the said means of emission comprise a layer comprising, at said area, at least two parallel conducting tracks, oriented along the said dipole direction and suitable for being able to be traversed in mutually opposite senses by an electric current;
  the said detection means comprise a layer comprising, at said area, at least one conducting track oriented along the said first direction of detection, and a layer comprising, at said area, at least one conducting track oriented along the said second direction of detection;
  the calculation means comprise:
    (Z) memory means suitable for containing a model of the area by at least two numerical parameters related to $\sigma^s$ representing the said electrical conductivity $\sigma$ in this area, and $\epsilon_r^s$ representing the said dielectric permittivity in this area, and a model of the said means of emission,
    (E) estimation means suitable for estimating a simulated component of a simulated electric field generated in the said model of the area by the said model of means of emission, along the said first direction of detection, and
    (F) comparison means suitable for comparing the said simulated component and the said corresponding measured component obtained by the means of detection (B);
  the calculation means comprise:
    (Z) memory means suitable for containing a model of the area by at least two numerical parameters related to $\sigma^s$ representing the said electrical conductivity $\sigma$ in this area, and $\epsilon_r^s$ representing the said dielectric permittivity in this area, and a model of the said means of emission, (E) estimation means suitable for estimating a first and a second simulated component of the said simulated electric field along the said first and second directions of detection, and (F) comparison means suitable for comparing the said simulated components and the said corresponding measured components obtained by the detection means (B);

the device furthermore comprises (D) generating means suitable for generating the said model contained in the memory means (Z);

the device furthermore comprises (G) a database containing data relating to an energy absorbed by a structural element exhibiting an electrical conductivity σ and a dielectric permittivity $\epsilon_r$ for the said materials;

the device furthermore comprises a layer for integrated monitoring of the structures based on piezoelectric technology;

the said structural element comprises no imperfectly conducting material, and the means of emission are means of emission of electrical radiation that are suitable for generating an electric field extending in the said direction.

According to another aspect, the invention relates to a structure suitable for health monitoring of an area of a structural element of the said structure, and comprising:

the said structural element comprising at least one dielectric material of dielectric permittivity $\epsilon_r$, an electromagnetic radiation emission layer extending in a direction, the said electromagnetic field generating an electric field in the area, a detection layer suitable for measuring a first measured component of an electric field, along a first direction of detection, and at least one facility for connection to calculation means suitable for obtaining a value of the dielectric permittivity $\epsilon_r$ in the said area on the basis of the said first measured component.

According to embodiments, recourse may also be had to one and/or other of the following arrangements:

the said structural element is an inhomogeneous structural element furthermore comprising an imperfectly conducting material, of electrical conductivity σ, in which the means of emission are means of emission of magnetic radiation that are suitable for generating a magnetic field, the said magnetic field being, at the level of the area, equivalent to a magnetic field emitted by a magnetic dipole extending in the said direction, and in which the calculation means are alternatively or furthermore suitable for obtaining a value of the electrical conductivity σ in the said area on the basis of the said first measured component;

the said structural element takes the form of at least one layer, the said detection layer being disposed between the said structural element layer and the said emission layer;

the said structural element takes the form of at least one layer, the said emission layer being disposed between the said structural element layer and the said detection layer;

the said structural element takes the form of at least one layer, the said structural element layer being disposed between the said emission layer and the said detection layer;

the said inhomogeneous structural element takes the form of at least one fine layer comprising at least one imperfectly conducting material in the form of at least one carbon fibre, of electrical conductivity σ, and one dielectric material in the form of a matrix of dielectric permittivity $\epsilon_r$, in which the said carbon fibres are embedded.

According to another aspect, the invention relates to a method for health monitoring of an area of a structural element comprising at least one dielectric material of dielectric permittivity $\epsilon_r$, comprising the steps during which:

(a) an electromagnetic field is generated, by means of emission of electromagnetic radiation extending in a direction, the said electromagnetic field generating an electric field in the area, and (b) a first measured component of an electric field is measured, along a first direction of detection, characterized in that the method furthermore comprises a step (c) during which a value of the dielectric permittivity $\epsilon_r$ in the said area is obtained on the basis of the said first measured component.

According to preferred embodiments, recourse may moreover be had to one and/or other of the following arrangements:

the said structural element is an inhomogeneous structural element furthermore comprising an imperfectly conducting material, of electrical conductivity σ, during step (a), a magnetic field is generated by means of emission of magnetic radiation, the said magnetic field being, at the level of the area, equivalent to a magnetic field emitted by a magnetic dipole extending in the said direction, and during step (c), a value of the electrical conductivity σ in the said area is alternatively or furthermore obtained on the basis of the said first measured component;

during a first iteration, steps (a) to (c) are performed for a first frequency of the emission means, during a second iteration, steps (a), (b) and (c) are repeated for a second frequency, and during step (c) of the second iteration, the value obtained during step (c) of a previous iteration is taken into account;

during each step (b), a second measured component of the said electric field is furthermore measured, along a second direction of detection forming with the said first direction a nonzero angle, and during step (c) of each iteration, the said first and second measured components are taken into account;

during step (c), for each iteration, furnished, in memory means, with an initial model of the area through at least two numerical parameters related to $\sigma^s$ representing the said electrical conductivity σ in this area, and $\epsilon_r^s$ representing the said dielectric permittivity in this area, and a model of the said emission means, (e) at least one first simulated component of a simulated electric field generated in the said model of the area by the said model of means of emission is estimated, along a direction of detection chosen from the said first and second direction of detection, and (f) the said simulated component and the said corresponding measured component obtained during step (b) are compared;

the method furthermore comprises, prior to step (e), a step
(d) in which an initial model of the area by at least two
numerical parameters related to $\sigma^s$ representing the said
electrical conductivity a in this area, and $\epsilon_r^s$ representing
the said dielectric permittivity in this area, and a model
of the said means of emission, are generated in the
memory means;

during step (b), a second measured component of the said
electric field is measured, along the other direction of
detection, during step (e), a second corresponding simulated component
of the said simulated electric field is estimated, and during step (f), the said second simulated component and
the said second measured component obtained during step (b)
are compared;

subsequent to step (f), step (d') is furthermore implemented, in which a modified model of the area is generated by at least two numerical parameters related to $\sigma^s$ representing the said electrical conductivity $\sigma$ in this area, and $\epsilon_r^s$ representing the said dielectric permittivity in this area, differing from the initial model through at least one of the numerical parameters, and steps (e) and (f) are implemented for the said modified model;

step (c) furthermore comprises a step (g) during which at least one characteristic of the area chosen from the conductivity $\sigma$ and the permittivity $\epsilon_r$ is determined by identifying the said simulated conductivity $\sigma^s$ with the said conductivity and/or the said simulated permittivity $\epsilon_r^s$ with the said permittivity, as soon as the comparison performed in step (f) gives a satisfactory result;

the method furthermore comprises a step during which (h) an energy absorbed by the said structural element exhibiting the said electrical conductivity $\sigma$ and/or the said dielectric permittivity $\epsilon_r$ that are obtained in step (c) is determined by inference on a database containing data pertaining to an energy absorbed by a structural element exhibiting an electrical conductivity $\sigma$ and a dielectric permittivity $\epsilon_r$ for the said materials;

the said structural element comprises no, even imperfectly, electrically conducting material, and, during step (a), an electric field is generated in the area, in the said direction, with the aid of means of emission of electrical radiation;

during step (c), furnished, in memory means, with an initial model of the area by at least one numerical parameter related to $\epsilon_r^s$ representing the said dielectric permittivity in this area, and a model of the said means of emission, (d) a simulated component of a simulated electric field induced in the said model of the area by the said model of means of emission is estimated, and (e) the said simulated component and the said corresponding measured component obtained during step (b) are compared.

DESCRIPTION OF THE FIGURES

Other characteristics and advantages of the invention will become apparent during the following description of one of its embodiments, given by way of nonlimiting example, with regard to the appended drawings.

In the drawings:

FIGS. 6a, 6b, 6c are diagrammatic views of the model used within the invention.

In the various figures, the same references designate identical or similar elements.

DESCRIPTION OF THE EMBODIMENTS

Figure 1:
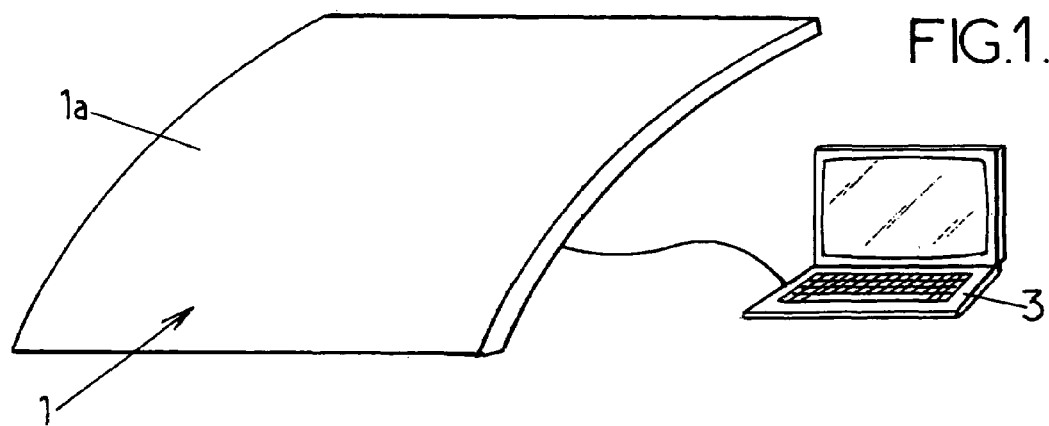
FIG. 1 is a perspective view of an instrumented structure.

FIG. 1 represents a structural element 1 which is typically a part of a structure embodied from a composite material of the type comprising a resin reinforced with carbon fibres. The structural element in question is, for example, a stiff element of the structure of a space, naval, automobile, railway or other vehicle, in which the composite materials find important applications, in particular by virtue of the saving in weight that they allow the structure to exhibit with respect to a metal structure exhibiting equivalent stiffness. Thus, the structural element 1 in question may be an entity undergoing manufacture, or otherwise, intended to be mounted in a complete structure, or may possibly be part of a complete structure in service.

The structural element 1 comprises a structure integrated monitoring device 2 (see the following figures) which is, for example, disposed on its internal face 1b, the external face 1a of the structural element being turned towards the outside space, and therefore, liable to be damaged during use of the vehicle comprising the structural element. The monitoring device 2 is thus used to evaluate the magnitude of the damage suffered by the structural element at its external face 1a. Such damage may be caused either in the normal use of the vehicle comprising the structural element, or deliberately during manufacture, during tests intended to study the resistance of the structural element intended to form part of the structure, or to verify the properties of the materials used during of the manufacture of the structural element.

This damage is typically of three distinct types, namely: damage of a mechanical origin, as a result for example of an impact, or damage of a thermal origin, as a result of a considerable rise in temperature suffered by the item, or of a chemical nature, following for example the absorption of a liquid.

The integrated monitoring device 2 has connection facilities suitable for linking it to a control unit 3 used to emit excitation signals towards the monitoring device, and to receive signals from this monitoring device, these signals being dependent on the possible damage to the structural element.

Figure 2:
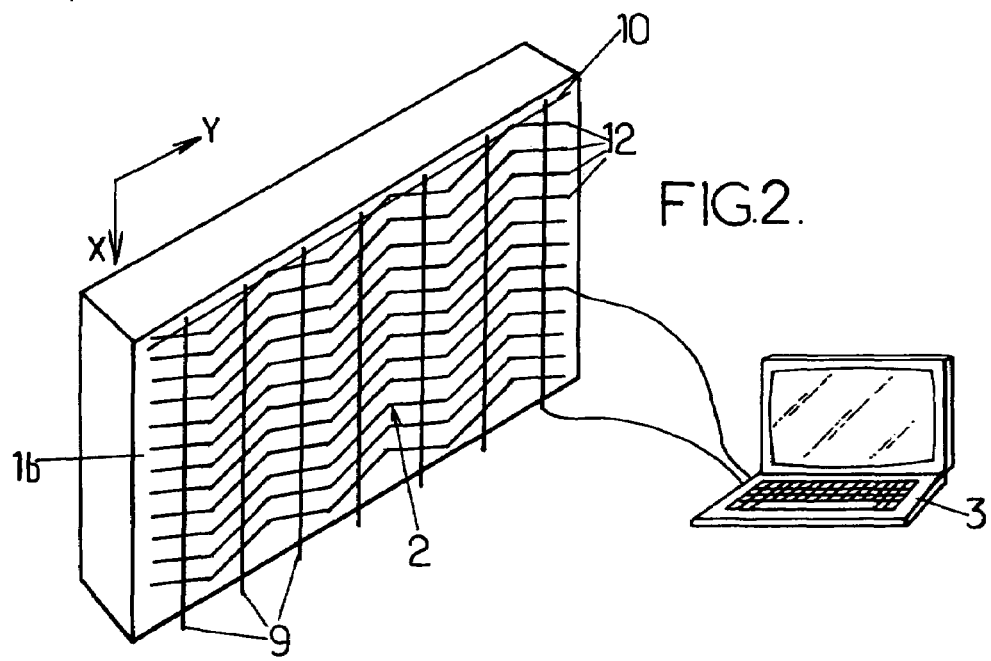
FIG. 2 is a perspective view of the internal face of an area of the structure presented in FIG. 1 furnished with a device according to the invention.

Reference is now made to FIG. 2 which represents in a diagrammatic manner an area of the structural element 1, furnished on its internal face 1b with the structure integrated monitoring device 2, according to an embodiment of the latter. The device as such takes the form of conducting tracks held in a mylar and fixed for example by gluing to the internal face 1b of the structural element. The device 2 comprises in particular an emission layer 4 (detailed later) comprising a plurality of parallel linear conducting tracks 9 extending along an axis X of the structural element, and linked together, for example at one end, by a conducting track 10, for example perpendicular. The device for integrated monitoring of structures also exhibits means of detection in the form of a detection layer 5, also comprising conducting tracks 12, and possibly taking the form of a plurality of variants as described in relation to FIGS. 5a, 5b and 5c. The emission layer 4 can be disposed between the structural element 1 and the detection layer 5 or, instead, it is the detection layer 5 which is disposed between the emission layer 4 and the structural element 1. The tracks of the emission layer 4 and of the detection layer 5 are linked to the central unit 3.

FIG. 2 represents a small enough portion of the structural element of FIG. 1 as to be locally regarded as planar in the plane (X; Y). The flexibility of the emission layer 4 and detection layer 5 allows them to be fixed, for example by gluing onto the internal face of the entire structural element 1, even if the latter exhibits a nonzero curvature, as represented in FIG. 1.

Figure 3:
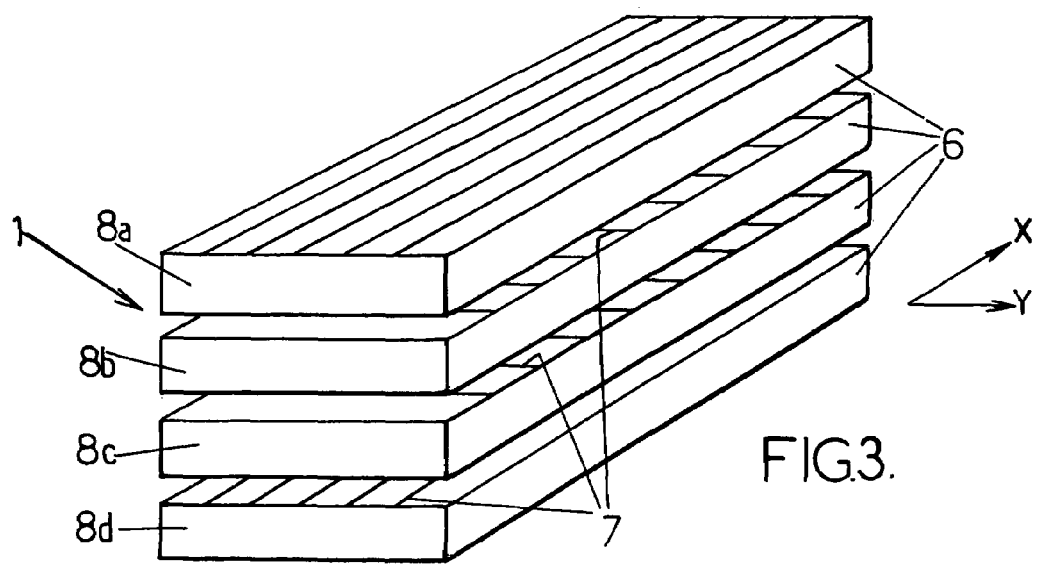
FIG. 3 is an exploded perspective view of a composite structure to which the invention is applicable.

FIG. 3 represents for example the structural element 1 in the form of a composite element consisting of a matrix 6, a dielectric material characterizable by its dielectric permittivity $\epsilon_r$, and of carbon fibres 7, or of any other suitable imperfectly electrically conducting material, characterizable by its electrical conductivity σ. In a conventional manner, the composite structural element 1 comprises several layers 8a, 8b, 8c, 8d in which the carbon fibres extend in different directions so as to give the structure an orthotropic character. The layers 8a and 8d thus exhibit carbon fibres extending in the direction X, while layers 8b and 8c exhibit carbon fibres extending in the direction Y.

The invention can also be used for quasi-isotropic structures in which the carbon fibres of successive layers form an angle of 45° between themselves, or any appropriate composite material based on imperfectly conducting material.

Figure 4:
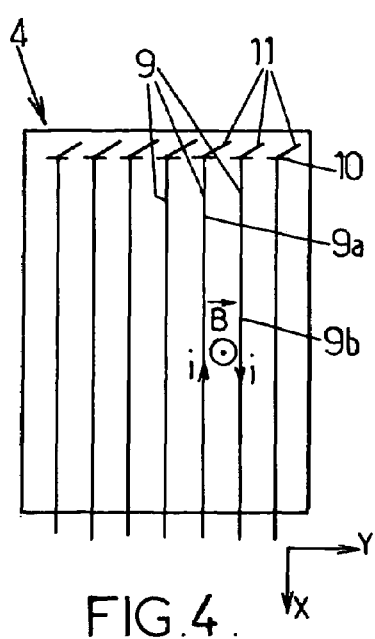
FIG. 4 is a plane diagrammatic view of a source of magnetic radiation used within the invention.

FIG. 4 diagrammatically represents the emission layer 4 fixed on the structural element 1 and comprising parallel electrically linear conducting tracks 9 extending in the direction X and linked together for example at one end by an electrically conducting track 10 possibly exhibiting a series of switches 11, and linked at their other end to the control unit 3. The control unit 3 can emit a current i into a conducting track 9a, the switch 11 associated with this conducting track 9a being closed, and the other switches 11 being open, so that the current also flows in the neighbouring conducting track 9b in the opposite sense from the current flowing in the conducting track 9a, in such a way as to form a loop generating in the structure a magnetic field B equivalent to the magnetic field generated by a magnetic dipole oriented along the X direction.

The current i emitted by the central unit 3 is preferably an alternating current generated successively at several frequencies as described in greater detail in what follows. The current in question is emitted successively into the various tracks 9 of the emission layer 4, and the corresponding switches may be open or closed in a manner suitable for being able to scan the structure 1 along the Y direction. Any other suitable means for scanning the structure may be used. All these operations are controlled by the central unit 3.

In a conventional manner, for hybrid integrated monitoring of structures, the magnetic field B emitted by the emission layer 4 generates in the imperfectly conducting structural element 1 eddy currents that form an electric field E detected by the detection layer 5.

Figure 5A:
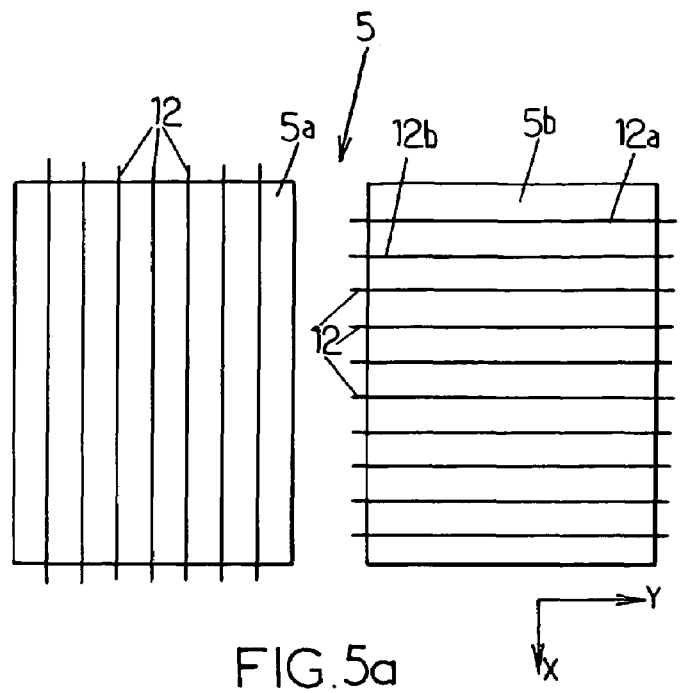
FIGS. 5a, 5b, 5c are plane diagrammatic views of various embodiments or of means of detection according to the invention.

FIG. 5a represents, for example, in a likewise diagrammatic manner, a first embodiment of such a detection layer 5 according to the invention. In this first embodiment, it is more judicious to speak of two detection layers 5a, 5b, intended to be placed one on the other, the layer 5b comprising a series of linear parallel conducting tracks 12 linked at one end to the central unit 3, and free at the other end, and disposed along the Y axis perpendicularly to the conducting tracks 9 of the emission layer 4. A detection layer 5b of this kind has already been described repeatedly, and in particular in the abovementioned article, and is suitable for detecting the component $E_y$, extending along the Y direction of the electric field E. The layer 5a is composed in a similar manner and exhibits conducting tracks 12 likewise linked to the control unit 3, but oriented along the X direction so as to detect the component $E_x$ of the electric field E. Let us also note here that the components $E_x$ and $E_y$ detected are defined by the orientation of the equivalent magnetic dipole at the level of the emission layer in the area under study, and that the orientation of the carbon fibres in the material is in this respect irrelevant.

The information measured by exciting the conducting fibres 9a and 9b of the emission layer 4 and the conducting tracks 12a and 12b of the detection layer 5 makes it possible to obtain information relating to $E_x$ and/or $E_y$ at the level of the "intersection" of these tracks. By exciting the various conducting tracks 9a, 9b in succession, then for each, by exciting the various conducting tracks 12a and 12b in succession, a complete mapping of the structural element 1 bearing the device for integrated monitoring of structures 2, even of large size, is thus obtained in a fraction of a second.

For each point scanned, the current emitted is an alternating current emitted successively at various frequencies, this making it possible to also scan the structure 1 depthwise. By scanning the structure at a high frequency, corresponding to the thickness of the surface layer of the structural element, information specific to this layer is obtained. By lowering the frequency to a frequency corresponding to the thickness of the first two layers, information relating to these two layers is obtained. By using the information obtained for the first layer, information about the second layer alone is obtained. By continuing thus, the structural element is scanned depthwise.

In practice, the damage suffered by the structure will have been suffered on its external face 1a, and the integrated monitoring device 2 will be disposed on its internal face 1b, in particular in such a way as to prevent any risk of damage of the integrated monitoring device, and it is therefore essential that the latter be capable of determining damage occurring "depthwise" with respect to itself. Hence, the iterative calculations can be performed layer by layer beginning with a low frequency to obtain information about the entire structure, then raising the frequency successively.

The inventors have noted that the detection of the component $E_y$ of the electric field traversing the structural element 1 made it possible to obtain additional information with respect to the sole detection of the component $E_x$ of the electric field. With the aid of the two independent components $E_x$ and $E_y$, it is possible by calculation to retrieve a value of the two characteristics of the material, namely the electrical conductivity $\sigma$ of the medium and the dielectric permittivity $\epsilon_r$ of the matrix.

The measured components may be real or complex of the form $E_x = E^0_x e^{j(\omega t + \phi)}$, thus carrying the amplitude information and phase information.

The separate calculation of the electrical conductivity $\sigma$ and of the dielectric permittivity $\epsilon_r$ is beneficial, since in its turn it makes it possible to characterize the type of defect that the structure may have suffered, between on the one hand the defects of a mechanical origin which give rise to delamination between layers and possibly rupture of the carbon fibres and thus solely a variation in the electrical conductivity $\sigma$, or on the other hand, the defects of a chemical or thermal origin that give rise to damage chiefly of the matrix and therefore a modification of the dielectric permittivity $\epsilon_r$ of the latter, and possibly of the conductivity $\sigma$ of the medium by pyrolysis of the resin. The benefit of being able to characterize the nature of the damage that the structure has suffered is of being able to forecast for example the type of intervention (repair) to be conducted on the structure.

The inventors have, furthermore, shown that this method made it possible to detect defects of a chemical and/or thermal origin with greater accuracy than the existing techniques for integrated monitoring of structures, which are more suited for measuring defects of a mechanical origin.

Of course, there are numerous other means, within the invention, for detecting the component $E_y$ of the electric field traversing the structure. In particular, two alternative embodiments of the detection layer are presented with reference to FIGS. 5b and 5c respectively.

Figure 5B:
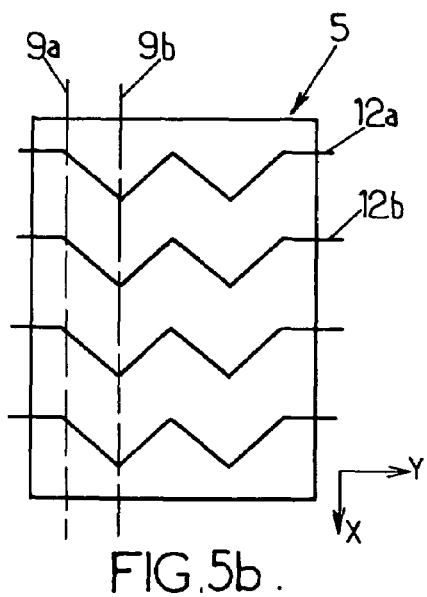

In FIG. 5b, the detection layer 5 is now formed only by a single layer which comprises a series of zigzag conducting tracks 12, the tracks 12a and 12b remaining parallel while forming these zigzags. In a purely illustrative manner, also represented in FIG. 5b are the conducting tracks 9a and 9b of the emission layer 4, said tracks being superposed on the detection layer 5 and excited by the central unit 3, and traversed by the current i. The central unit 3 may then read at the level of the conducting tracks 12a and 12b information relating to $E_x + E_y$ if the zigzags are oriented by 45° with respect to the X and Y direction. This embodiment is the embodiment illustrated in FIG. 2 globally representing the structure and likewise the emission layer 4.

Figure 5C:
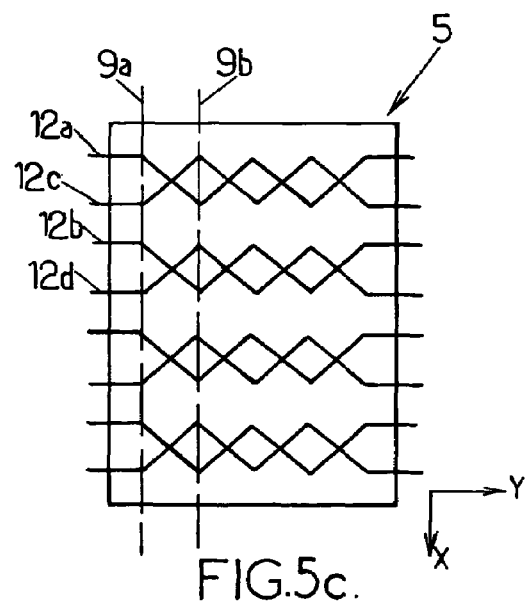

According to a third embodiment represented in FIG. 5c, the embodiment of FIG. 5b is again employed for the detection layer 5 and it is supplemented with a series of pairwise parallel conducting tracks 12c, 12d, superposed respectively on the conducting track 12a and on the conducting track 12b according to an inverse zigzag, so that while the conducting tracks 12a and 12b make it possible to obtain information relating to $E_x + E_y$, the parallel conducting tracks 12c and 12d make it possible to obtain for the same excited conducting tracks 9a, 9b of the emission layer 4 information relating to the component $E_x - E_y$ of the electric field. By combining these items of information, the components $E_x$ and $E_y$ will be retrieved directly, separately.

It is of course not obligatory for the zigzags formed by the conducting tracks 12a, 12b, 12c, 12d in any of the embodiments presented, to form an angle of 45° with the X and Y directions such as defined by the orientation of the conducting tracks 9 of the emission layer 4, and it is possible to choose any angle whatsoever. Furthermore, although the zigzags of the conducting tracks 12a to 12d are represented at right angles, it is permissible for the conducting tracks in question to exhibit rounded angles for reasons of practical implementation.

The signal detected at the level of the conducting tracks 12 of the detection layer by the central unit 3 is possibly processed by well-known signal processing algorithms such as already used in the field of the integrated monitoring of structures, such as for example the Donoho algorithm cited in the abovementioned article. Such signal processing may, in fact, be useful for circumventing the various noise terms carried by the signal.

The device as described makes it possible to obtain quantitative results regarding the state of health of structures, for example by comparing the results obtained with results obtained previously for the structure in question, for example when bringing the structure into service, or during an earlier examination if the structure is scanned periodically. The comparing of the detection results with previous detection results makes it possible to determine the occurrence and the nature of any damage suffered by the structure.

It is, moreover, possible to quantify the level of damage, as described subsequently with the aid of a model suitable for calculating the electric field for the structure under study, at the level of the detection layer.

In order to do this, use is made, in the central unit 3, of a model of the structure, which may for example have been previously devised at the time the structure was brought into service. This model is in particular suitable for the application thereto of the DPSM method (the acronym standing for the expression Distributed Point Source Method) which will be detailed in a general manner with the aid of FIGS. 6a, 6b, and 6c. This method is particularly suitable in that it makes it possible to obtain information relating to a point (or a limited part) of space in short computation times. This said, there is nothing preventing the device described above from being used with a classical method of computation of the "finite elements" kind.

Reference is firstly made to FIG. 6a, in which a first surface b is meshed according to a plurality of surface samples such as dS'1, dS'2, dS'3 and dS'4. Likewise a second surface a is meshed by a plurality of surface samples such as dS1, dS2, dS3, dS4, etc.

Referring to FIG. 6b, with each surface sample $dS_i$ is associated a hemisphere $HEM_i$ tangent to the surface sample $dS_i$ at a point of contact $P_i$. Preferably, this point of contact $P_i$ corresponds to the apex of the hemisphere $HEM_i$.

During this step of meshing of the surfaces b and a, the surface area of the structural element is evaluated on the one hand and on the other hand a number of surface samples $dS_i$ is chosen according to the desired position of the estimation of the electric field. Thus, the surface area of a sample $dS_i$ is given by $S_0/N$ where $S_0$ corresponds to the total surface area of the surface b to be studied, and N corresponds to the chosen number of surface samples $dS_i$.

The hemisphere $HEM_i$ has the same surface area as the sample $dS_i$. Thus, the radius $R_i$ of the hemisphere is deduced from the expression $2\pi R_i^2 = S_0/N$.

Each mesh cell represented by a surface sample $dS_i$ exhibits, in the example described, a parallelogram shape, with centre $P_i$ corresponding to the point of intersection of the diagonals of this parallelogram.

The hemisphere $HEM_i$ is tangent to the surface sample $dS_i$ at this point $P_i$. Of course, the mesh cells may be of various shapes, triangular or otherwise. It is indicated in a general manner that the point $P_i$ corresponds to the barycentre of the mesh cell.

It may be useful to restart directly from a mesh of the structural element developed during the design of the structure.

When the boundary conditions of the problem pertain to a vector quantity, three sources $SA_i$, $SB_i$, $SC_i$ are assigned to the surface sample $dS_i$.

The three sources $SA_i$, $SB_i$, $SC_i$, allocated to a surface sample $dS_i$ have respective positions determined as indicated below. As represented in FIG. 6b, the three sources $SA_i$, $SB_i$, $SC_i$ are coplanar and the plane comprising these three sources furthermore comprises the base of the hemisphere $HEM_i$. The hemisphere $HEM_i$ is constructed with the centre of the disc constituting the base of the hemisphere which corresponds to the barycentre of the three sources $SA_i$, $SB_i$, $SC_i$.

Figure 6C:
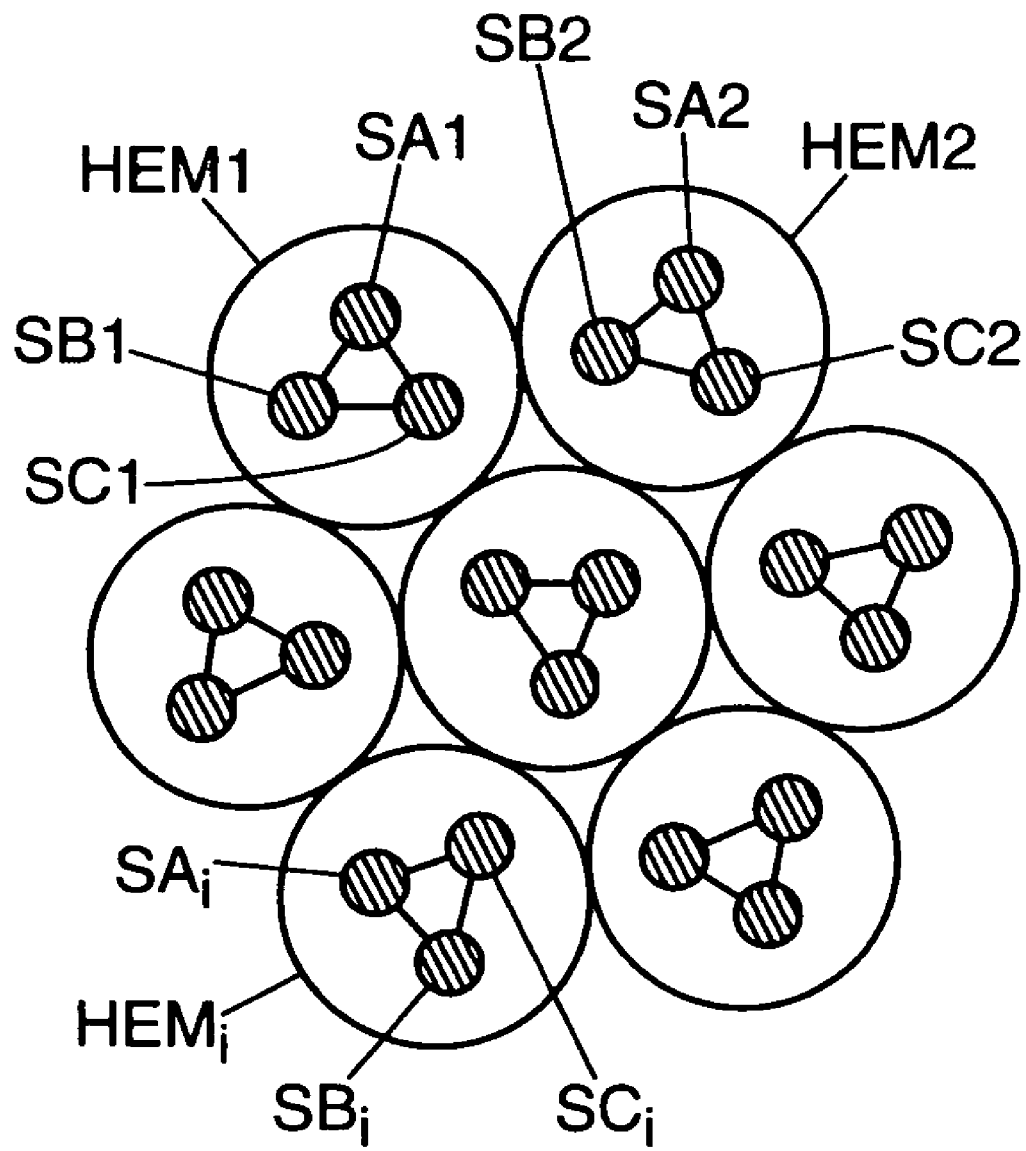

For a neighbouring hemisphere $HEM_2$, the three sources $SA_2$, $SB_2$, $SC_2$ may be oriented in a different manner from the sources $SA_1$, $SB_1$, $SC_1$ of the hemisphere $HEM_1$, as represented in FIG. 6c, and as a general rule, the sources of the various hemispheres may be oriented in a random manner so as to avoid an overperiodicity phenomenon.

It is considered that the sources $S'_{A1}, \ldots, S'_{CN}, S_{A1}, \ldots, S_{CN}$ are fictitious charges emitting an excitation field into the structure.

The electric field at any points $M_1, \ldots, M_N$ of the medium are related to the intensities of the charges of the sources of the points $A_1, \ldots, A_N, B_1, \ldots, B_N, C_1, C_N$ by the following expression:

$$\begin{pmatrix} V_x(M_1) \\ V_x(M_2) \\ \vdots \\ V_x(M_N) \\ V_y(M_1) \\ V_y(M_2) \\ \vdots \\ V_y(M_N) \\ V_z(M_1) \\ V_z(M_2) \\ \vdots \\ V_z(M_N) \end{pmatrix} = F'(M) \cdot \begin{pmatrix} v'A_1 \\ v'A_2 \\ \vdots \\ v'A_N \\ v'B_1 \\ v'B_2 \\ \vdots \\ v'B_N \\ v'C_1 \\ v'C_2 \\ \vdots \\ v'C_N \end{pmatrix} \quad [1]$$

where:
the coefficient $v'_{\Sigma j}$ ($\Sigma = A, B, C$ and $j = 1, 2, \ldots, N$) of the first column matrix corresponds to the value of electric charge $q_j$ for the source $S'_{\Sigma j}$;
the coefficients $V_u(M_i)$ (where $u = X, Y, Z$ and $i = 1, 2, \ldots, N$) of the second column matrix correspond to a value of the electric field at a point $M_i$ of space;

the interaction matrix $F'$, of dimension $3N \times 3N$ is expressed by the relation:

$$F' = \begin{pmatrix} \overline{N\{C_A^x(i,j)} & \overline{C_B^x(i,j)} & \overline{C_C^x(i,j)} \\ N\{C_A^y(i,j) & C_B^y(i,j) & C_C^y(i,j) \\ N\{C_A^z(i,j) & C_B^z(i,j) & C_C^z(i,j) \end{pmatrix} \quad [2]$$

The expression for these coefficients is as follows:

$$C_\Sigma^u(i,j) = f_u[d(P_i, S_{\Sigma,j})] \text{ with} \quad [3]$$

$$\Sigma = A, B, C \quad [4]$$
$$i = 1, 2, \ldots, N$$
$$j = 1, 2, \ldots, N$$
$$u = x, y, z.$$

$$C_\Sigma^u(i,j) = \left[ -\overline{grad}\left(\frac{1}{2\pi\varepsilon \overline{M_i S_{\Sigma j}}}\right) \right]_u,$$

where
$\varepsilon = \varepsilon_r \cdot \varepsilon_0$ corresponds to the dielectric permittivity of the medium wherein the point $M_i$ is situated.

Thus, the matrix system of equation 1 makes it possible to estimate, on the basis of an interaction matrix $F'$ and of a vector comprising the values $v'_{\Sigma j}$ associated with the sources $S'_{\Sigma j}$, the coefficients of a vector (column matrix) comprising the values of the electric field $V(M_i)$ at the point in space $M_i$.

To determine the values of the sources $v'_{\Sigma j}$, the matrix system of equation 1 is applied to the points $P'_1, \ldots, P'_N$ corresponding to the apex of the hemispheres $HEM_i$ of the surface b, where the incident electric field can be known. The values of the sources $v'_{\Sigma 1}, v'_{\Sigma 2}, \ldots, v'_{\Sigma N}$ are thus determined by the following equation:

$$\begin{pmatrix} v'_{A1} \\ \vdots \\ v'_{AN} \\ v'_{B1} \\ \vdots \\ v'_{BN} \\ v'_{C1} \\ \vdots \\ v'_{CN} \end{pmatrix} = F'(P')^{-1} x \begin{pmatrix} V_x(P'_1) \\ \vdots \\ V_x(P'_N) \\ V_y(P'_1) \\ \vdots \\ V_y(P'_N) \\ V_z(P'_1) \\ \vdots \\ V_z(P'_N) \end{pmatrix} \quad [5]$$

where the coefficients of $F'^{-1}(P')$ are determined since the respective distances from the points $P'_1, \ldots, P'_N$ to the points $A_1, \ldots, C_N$ are known.

Once these values of sources $v'_{\Sigma j}$ have thus been determined, the expression for the electric field $V'$ at any point $M$ in space is easily calculated.

By referring again to FIG. 6a, it will be understood that the second surface a receiving the wave emitted by the first surface b acts, itself, as an active surface re-emitting a secondary wave by reflection. Each source $S_{\Sigma i}$ represents a contribution to the emission of this secondary wave.

To take account both of the presence of the main wave and of the presence of the secondary wave at the points M, the contribution of the main wave and the contribution of the secondary wave at the point M is estimated by the matrix system:

$$V'(M) = F \times \begin{pmatrix} v_{A1} \\ v_{A2} \\ \vdots \\ v_{AN} \\ v_{B1} \\ v_{B2} \\ \vdots \\ v_{BN} \\ v_{C1} \\ v_{C2} \\ \vdots \\ v_{CN} \end{pmatrix} + F' \times \begin{pmatrix} v'_{A1} \\ v'_{A2} \\ \vdots \\ v'_{AN} \\ v'_{B1} \\ v'_{B2} \\ \vdots \\ v'_{BN} \\ v'_{C1} \\ v'_{C2} \\ \vdots \\ v'_{CN} \end{pmatrix} \qquad [6]$$

where:

F is the matrix of interaction between the surface a and the points M;

$v_{\Sigma j}$ ($\Sigma=A, B, C$; $j=1, 2, 3, \ldots, N$) is the value of the sources allocated to each surface sample $dS_j$ of the surface a, N being the total number of mesh cells chosen for this surface.

The coefficients of the matrix F are dependent on the distance $MS_{\Sigma j}$ where $S_{\Sigma j}$ are the sources assigned to each sample $dS_j$ of the second surface a.

In the case where the field emitted by the second surface is the reflection of the field emitted by the first, the values of the sources $v_{\Sigma j}$ of the second surface a are determined as a function of values of the sources of the first surface b, as is detailed below with reference to FIG. 7.

A value of reflection coefficient is assigned to each point $P_i$ of the second surface a.

In the particular case of a material made of carbon fibres embedded in a resin, this reflection coefficient is in particular dependent on the modelled electrical conductivity $\sigma^S$ of the carbon fibres at this point and the modelled dielectric permittivity $\epsilon^S_r$ of the resin at this point. A matrix $R_a$ which is representative of the reflection coefficient at each point $P_i$ is therefore introduced. At each point, $$R_a = \frac{1 - \left(\varepsilon_r - j\frac{\sigma}{\omega\varepsilon_0}\right)}{1 + \left(\varepsilon_r - j\frac{\sigma}{\omega\varepsilon_0}\right)}, \qquad [7]$$

where j is the complex number such that $j^2 = -1$, $\omega$ is the angular frequency of the incident field, $\epsilon_r$ the relative dielectric permittivity of the material and $\epsilon_0$ the dielectric permittivity in vacuo.

In what follows, it is indicated that:

$F(P_i)$ is the interaction matrix for the second surface a applied to the point $P_i$ of the second surface;

$F(P'_i)$ is the interaction matrix for the second surface applied to the point $P'_i$ of the first surface;

$F'(P_i)$ corresponds to the interaction matrix for the first surface applied to the point $P_i$ of the second surface;

$F'(P'_i)$ corresponds to the interaction matrix for the first surface applied to the point $P'_i$ of the first surface;

v' corresponds to the column vector comprising the values of the sources $S'_{\Sigma i}$ of the first surface; and v corresponds to the column vector comprising the values of the sources $S_{\Sigma i}$ of the second surface.

At the level of the second surface of the structural element 1, the contribution of the incident wave emitted by the first surface b is expressed by:

$$\vec{V'}(P) = F'(P) \cdot \vec{v}' \qquad [8]$$

The contribution of the secondary wave returned by the second surface a is expressed, by definition, by the relation:

$$\vec{V}(P) = F(P) \cdot \vec{v} \qquad [9]$$

Figure 7:
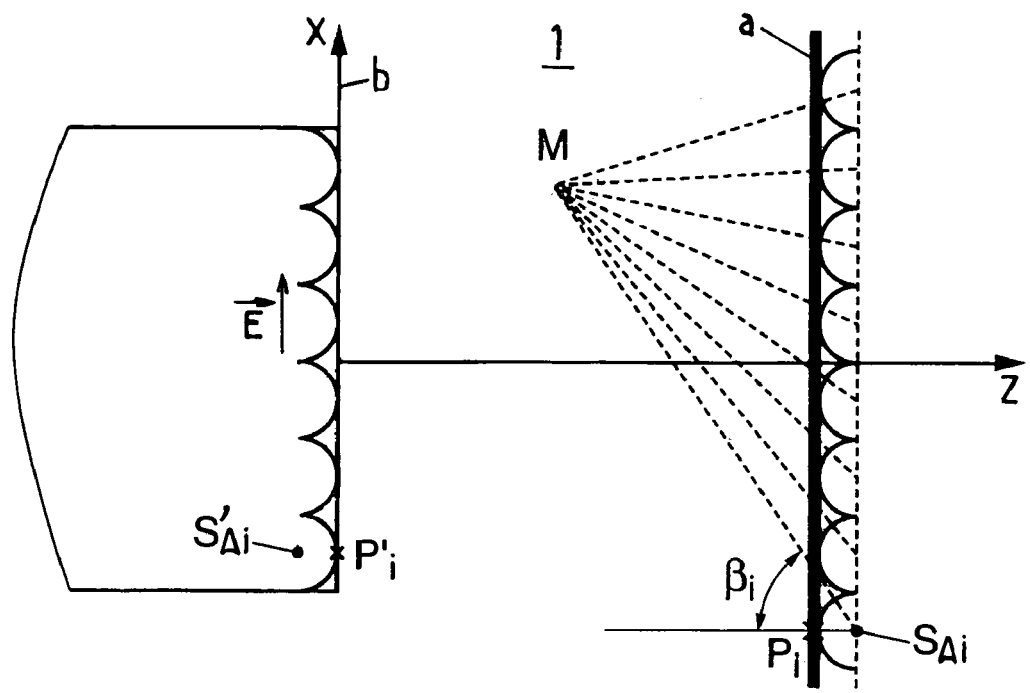
FIG. 7 is a diagrammatic side view representing the calculation of the electric field in a medium, within the invention.

Now, in the example represented in FIG. 7, the secondary wave corresponds simply to a reflection of the main wave, this being expressed by the relation:

$$\vec{V}(P) = R_a \vec{V'}(P) \qquad [10]$$

where $R_a$ corresponds to a reflection matrix each coefficient of which represents the contribution to the emission, by reflection, of the secondary wave, by each source $S_{\Sigma i}$ of the second surface.

From the three relations above we deduce the expression for the column vector v comprising the values of the sources on the second surface, on the basis of the column vector v' comprising the values of the sources of the first surface b by the relation:

$$\vec{v} = [F(P)]^{-1} \cdot R_a \cdot [F'(P)] \cdot \vec{v}' \qquad [11]$$

Thus, the value of the field V' (P') on the first surface b is determined directly as a function of the values of the sources v' of the first surface b in the case where the initial electric field is emitted over a single surface of the structure under study.

Figure 8:
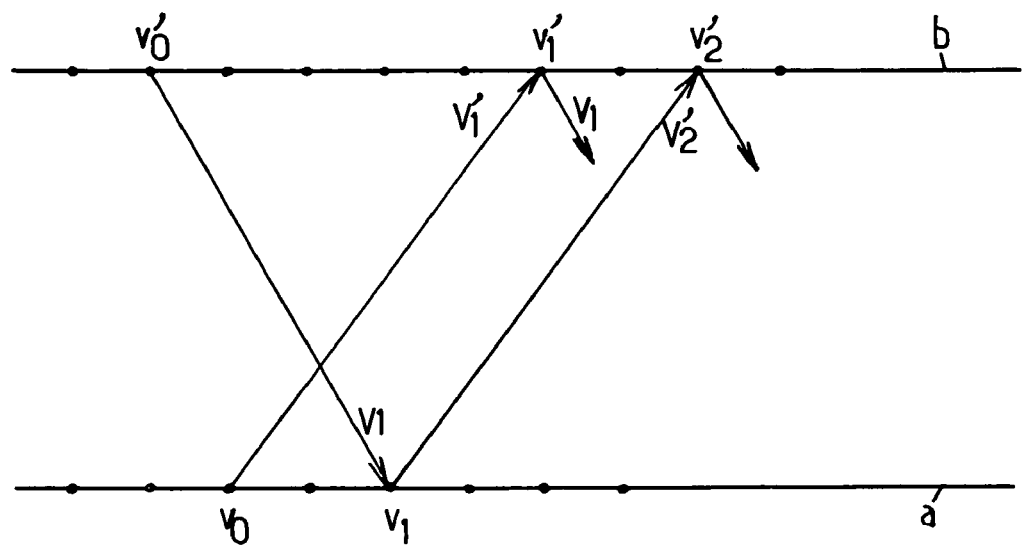
FIG. 8 is a diagrammatic figure representing the calculation of the effective sources in a structure.

FIG. 8 presents in a general manner the case of the calculation of the equivalent sources for a structure 1 subjected to an electric field simulated by initial charges $v'_0$ on the surface b and $v_0$ on the surface a.

In a general manner, if an exterior field is also applied to the second surface, then superposed on Equation 11 is Equation 6 applied to the sources of the second surface: V'(P')=F'(P')v'.

In a general manner, the field reflected on the second surface a of the structure will again be reflected on the first surface b as if emitted by sources $v'_2$ according to:

$R_b V'_2(P') = F'(P') v'_2,$ i.e. $v'_2 = F'^{-1}(P') R_b V'_2(P'),$

Or again $v'_2 = F'^{-1}(P') R_b F(P) v_1$      [12]

$v_1$ are the sources of a field itself corresponding to a reflection of the field emitted by the original sources $v'_0$ according to:

$R_a V_1(P) = F(P) v_1,$ i.e. $v_1 = F^{-1}(P) R_a V_1(P),$ or again $v_1 = F^{-1}(P) R_a F(P') v'_0$      [13]

By combining [12] and [13], we obtain the fictitious source $v'_2$ as a function of the initial source $v'_0$ according to:

$v'_2 = F'^{-1}(P') R_b F(P) F^{-1}(P) R_a F(P') v'_0.$

We can write $v'_2 = B\,A\,v'_0$, with the matrices $A = F^{-1}(P)\,R_a\,F(P')$ and $B = F'^{-1}(P')\,R_b\,F'(P)$.

Likewise on the exterior surface a, $$v_2 = F^{-1}(P) R_a F(P') F'^{-1}(P') R_b F(P) v_0,$$

i.e. $v_2 = A B v_0$.

The effective source corresponds to the sum of the various terms originating from the various reflections:

$$V_{Total} = v_0 + v_1 + v_2 + \ldots,$$

$$V_{Total} = v_0 + A v'_0 + AB v_0 + \ldots$$

By similarly writing the sources $v'_{Total}$ on the other surface, these two equations can be grouped together in the form:

$$\begin{pmatrix} v_{Total} \\ v'_{Total} \end{pmatrix} = \left[ \begin{pmatrix} 1 & 0 \\ 0 & 1 \end{pmatrix} + \begin{pmatrix} 0 & A \\ B & 0 \end{pmatrix} + \begin{pmatrix} AB & 0 \\ 0 & BA \end{pmatrix} + \begin{pmatrix} 0 & ABA \\ BAB & 0 \end{pmatrix} + \ldots \right] \begin{pmatrix} v_0 \\ v'_0 \end{pmatrix} \quad [14]$$

i.e. $\begin{pmatrix} v_{Total} \\ v'_{Total} \end{pmatrix} = P \begin{pmatrix} v_0 \\ v'_0 \end{pmatrix}.$ In practice, one will be limited to a finite number of reflections, corresponding to a finite number of terms for the matrix P, since each reflected field is of course attenuated with respect to the incident field. In practice one will choose not to consider any reflection, i.e.

$$P = \begin{pmatrix} 1 & 0 \\ 0 & 1 \end{pmatrix},$$

one reflection, i.e.

$$P = \begin{pmatrix} 1 & A \\ B & 1 \end{pmatrix},$$

or more, depending on the nature of the material, the thickness considered, the desired accuracy of the result, among other things.

Finally, the electric field V is calculated at the points chosen as a function of the initial sources $$\begin{pmatrix} v_0 \\ v'_0 \end{pmatrix}$$

by the formula:

$$\begin{pmatrix} V \\ V' \end{pmatrix} = \begin{pmatrix} F'(P') & F(P') \\ F'(P) & F(P) \end{pmatrix} \begin{pmatrix} v_{Total} \\ v'_{Total} \end{pmatrix} = M_0 P \begin{pmatrix} v_0 \\ v'_0 \end{pmatrix}, \text{ where} \quad [15]$$

$$\begin{pmatrix} F'(P') & F(P') \\ F'(P) & F(P) \end{pmatrix} = M_0.$$

Thus, the potential at any point in space lying between the surfaces a and b can be calculated as a function of the value of the initial sources $v_0$ and $v'_0$.

The DPSM technique just described may be used in three different ways.

Figure 9:
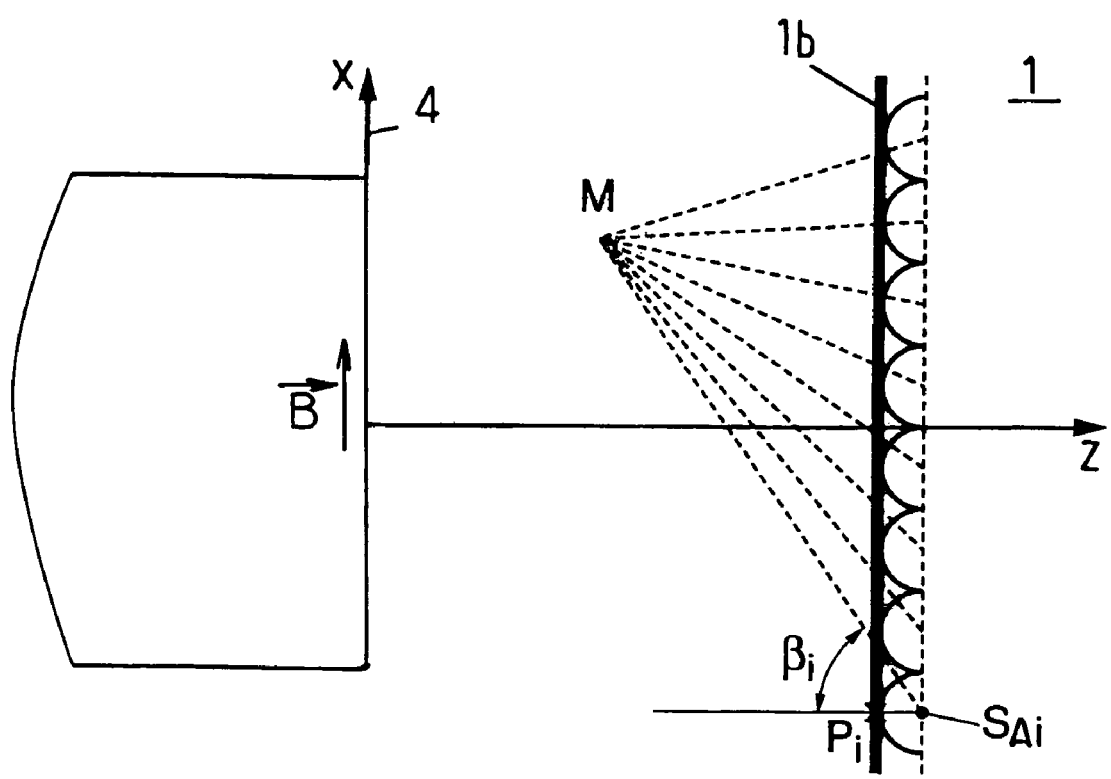
FIG. 9 is a diagrammatic side view representing the calculation of the electric field in a medium 1 within the framework of the invention.

I/ FIG. 9 represents the application of the above concepts to the case where the first surface b is the emission layer 4, the second surface a is the internal face 1b of the structural element 1, the medium being air or a resin in which the tracks of the detection layer 5 are held. One seeks to calculate the electric field at the point M of the detection layer 5.

As the expression for the current i traversing the emission layer 4 is known, it is possible to analytically calculate, for example by the Biot and Savart law, the incident electric field on the internal face 1b of the structural element. The reflection coefficient is applied to the incident field to determine the reflected field. The value of the sources $S_{A1}, \ldots, S_{CN}$ situated in the structural element and corresponding to elemental charges emitting the electric field reflected at the level of the face 1b is then calculated. The value of the electric field at the points M of the detection layer like the electric field emitted by these sources is next calculated by the DPSM method.

Figure 10:
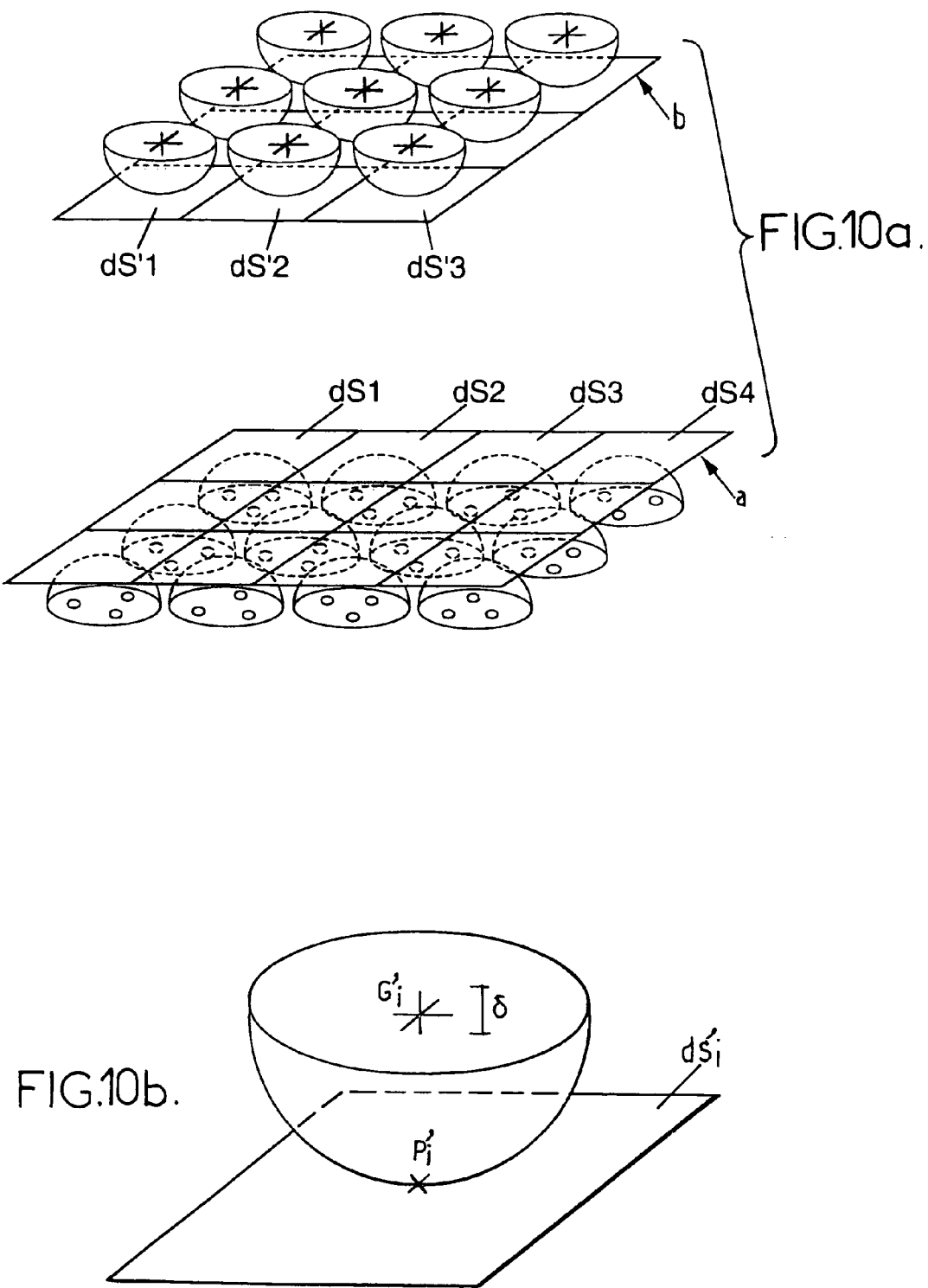
FIGS. 10a and 10b represent an alternative to the electric field calculation at the level of the internal face 1b of the structure.

Alternatively, recourse may be had to a DPSM modelling of the emission layer 4, as represented in FIGS. 10a and 10b. The emission layer 4 is modelled by elements each comprising a sphere exhibiting three current elements dI of length δ, intersecting the centre $G'_i$ of the base of the sphere so as to form a trihedron there. The orientation of the trihedrons may possibly vary from one element to another, to avoid overperiodicity problems. The length of each element is related to the diameter of the sphere and is calculated as a function of the boundary conditions imposed by the conducting tracks present at the level of the emission layer, or more generally by knowing at the points $P'_i$ the incident field due to an emission device.

Likewise, the incident electric field at the level of the internal face 1b is calculated by DPSM method on the basis of the values of the currents traversing the current elements. Then, the electric field is calculated in the detection layer as previously, on the basis of the reflection coefficient.

To summarize, one proceeds as follows:
the position of the points $P_i$ and of the sources $S_i$ is determined after meshing the faces;
the coefficients of the matrix F(P) are determined;
the coefficients of the reflection matrix $R_a$ are determined as a function of a reflection law of the obstacle;
the values of the vector V(P) at the points Pi of the internal face 1b are determined as a function of the boundary conditions on the internal face 1b, for which the incident electric field can be calculated, and the values of the sources $S_{\Sigma i}$ of the internal face 1b are deduced from the aforesaid values;
once the values of all the sources $S_{\Sigma i}$ have been determined, the matrix system given by relation 1 may be applied to every point M of the detection layer, by applying the interaction matrix F (involving the position of the point M and the positions of the respective sources $S_{\Sigma i}$) to this point M.

The model thus developed can be used jointly with the device for integrated monitoring of structures 2 to quantify the damage suffered by the structure.

Figure 11:
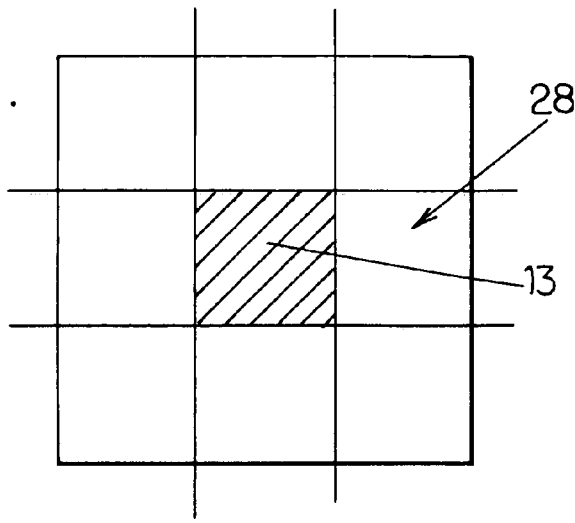
FIG. 11 is a plane diagrammatic view of a model of damage of the structure under study.

To do this, if it is detected that the structure has suffered damage, for example because a difference is noted between the measured components $E_x$ and $E_y$ of the electric field at the level of the detection layer 5 with the same electric field components measured previously, such as during a previous inspection, or by comparison with values contained in a database and established during manufacture of the structure, one can proceed as follows:

We start from a model of the healthy structure, which is contained in the control unit 3 and is established for example when the structure is brought into service. This model exhibits, by way of example, a modelled electrical conductivity $\sigma^s{}_0 = 10^4$ S.m$^{-1}$, and a modelled dielectric permittivity $\epsilon^s{}_{r0} = 4$, or any other preestablished values for the matrix and the fibres used. The model can be modified simply by modifying the reflection matrix $R_a$, simply by modifying one or the other of the said parameters $\sigma^s$ and $\epsilon_r^s$ at the level of the presumed damage suffered by the structure (location identified by the structure integrated monitoring device 2). The model thus established is represented in FIG. 11, where a healthy area 28 surrounding a damaged area 13 are represented diagrammatically.

Figure 12:
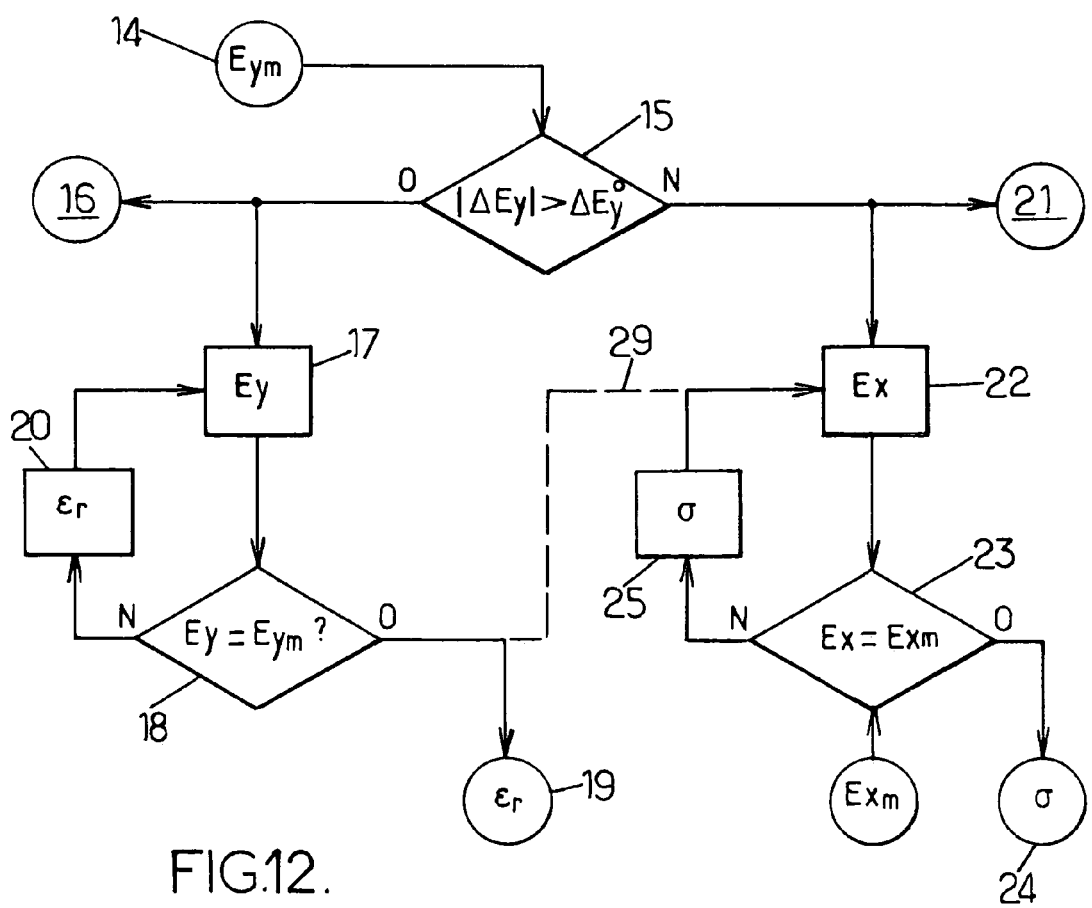
FIG. 12 is a schematic representative of the calculation of $\sigma$ and/or $\epsilon_r$ for the structure under test.

Purely mechanical damage having little influence on the component $E_y$ of the electric field detected (with of course the orientation represented in the figures), it is in particular possible to implement the algorithm proposed in FIG. 12.

Starting, at 14, from a measurement of the component $E_Y$ of the electric field, this component $E_{Ym}$ is compared, at 15, with a previous value of $E^0{}_{Ym}$, for example obtained during a previous examination, and contained in a database.

If the difference $\Delta E_Y = E_{Ym} - E^0{}_{Ym}$ is significant, for example greater than a preestablished threshold $\Delta E_y{}^0$ we can forthwith at this juncture conclude at 16 that there is a defect of a nonmechanical origin, namely a chemical and/or thermal origin in the structure and that has given rise to a variation in the dielectric permittivity $\epsilon_r$ of the resin. At 17, the component $E_y$ of the electric field is calculated for the model of the structure exhibiting a defect corresponding to a local variation in the permittivity $\epsilon_r$, having fixed for example $\epsilon_{rd} = 2$. At 18, the component $\epsilon_Y$, calculated at 17 for this model exhibiting a defect, is compared with the component $E_{Ym}$ measured by the structure integrated monitoring device 2. If the difference between these two values is less than a predetermined threshold, fixed for example by experience, then the value $\epsilon_r$ of the structure is deduced from this, at 19, as being that used in the model at 17. Otherwise, the model is modified at 20 by locally modifying the value of $\epsilon_{rd}$ assigned to the defect, and the calculation is redone at 17. It is thus possible to do a certain number of calculations so as to get closer to the value of dielectric permittivity actually present in the structure at the level of the defect, until the condition 18 is finally complied with.

Returning to the level of the comparison 15 between the measured value $E_{Ym}$ and a previously measured value of the same component, if no notable differences are apparent between these two components, and if there is nevertheless a difference between the measured component $E_{Xm}$ and a previously measured component $E^0{}_{Xm}$ for the structure, a defect of a mechanical origin can be concluded at 21 for the structure. Likewise, at 22 a component $E_X$ is calculated for the model exhibiting a defect of a mechanical origin, such as for example a conductivity $\sigma^s{}_d = 10^2$ S.m$^{-1}$, and the component calculated for the model of the structure exhibiting a defect and the measured component are compared at 23. If the difference between the measured component $E_{Xm}$ and the component calculated for the model of the structure exhibiting a defect is less than a certain predetermined threshold, we deduce from this, at 24, that the value of the electrical conductivity of the structure at this point is about equal to the value of the electrical conductivity used in the model at 22. Otherwise, the model is modified at 25, in particular by modifying the value of the electrical conductivity $\sigma_d$ at the level of the defect, and the component $E_X$ is calculated again at 22, for the modified model. It is thus possible to carry out a certain number of iterations until a calculated component $E_X$ is obtained which is close to the measured component $E_{Xm}$ of the electric field, and to deduce therefrom the value of the electrical conductivity of the area of the, structure equal to the value of $\sigma$ used during the last iteration of the model.

Once the component $E_X$ has been successfully identified at 23, it is possible to verify that the structure does not additionally exhibit a defect of a chemical and/or thermal origin. To do this, the component $E_Y$ calculated for the defect of a mechanical origin, is compared at 29 with the measured component $E_{Ym}$. Should there be a difference, the dielectric permittivity of the structural element under test is calculated in the same way as previously (17-19).

It is moreover possible to employ a database in which, for a structure equivalent to the structure under test, the modifications of the electrical conductivity $\sigma$ and/or the dielectric permittivity $\epsilon_r$ respectively have been measured for defects following monitored inputs of energy of a mechanical, chemical and/or thermal nature. On the basis of the values obtained at 19 and 24, it is thus possible, with the aid of this database, to get back to the energy undergone by the structure, and to deduce therefrom the energy received by the structure. It is thus possible to objectively determine whether the tolerance threshold for the structure has not been reached, or whether it is essential to envisage a repair and/or a replacement.

II/ In the foregoing, the calculations were performed outside of the structural element, the latter influencing the calculation only through the matrix $R_a$ of reflection at its surface. Nevertheless, the DPSM method can be used to more accurately represent the internal physical phenomena within the structure. In this case, FIG. 6a and FIG. 8 are employed again, in which the surface b corresponds to the internal face 1b of the structural element 1, the surface a corresponds to the external face 1a of the structural element 1, and the medium corresponds to the structural element 1, regarded as homogeneous through its thickness. A portion of the electric field incident on the internal face 1b, calculated analytically as before, is transmitted within the structural element 1. The field transmitted in the structural element is calculated by applying a transmission coefficient T (related to the ratio of the transmitted wave to the incident wave while the reflection coefficient R is related to the ratio of the reflected wave to the transmitted wave) to the incident field calculated analytically or by DPSM as previously. The initial sources $S'^0{}_{\Sigma i}$ correspond to sources emitting into the structural element the transmitted portion of the electric field incident on the face 1b from the emission layer 4. The initial sources $S^0{}_{\Sigma i}$ are zero, since no emission layer is employed on the external face 1a of the structural element. The effective sources $S_{\Sigma i}$ and $S'_{\Sigma i}$ are calculated by formula [14] and the electric field at every point of a medium by formula [15], choosing an appropriate number of reflections. When there are multiple reflections, the wave incident on the internal face 1b from inside the structural element 1 is also partially transmitted. Finally, the electric field in the detection layer is calculated as in relation to FIG. 9, with the aid of electric field sources emitting towards the detection layer the electric field transmitted towards the detection layer from the field incident on the face 1b from inside the structure 1, and of the local coefficient of transmission T' of the structural element towards the outside. The optimization calculation presented in relation to FIGS. 11 and 12 is then applied.

III/ The DPSM method also makes it possible to carry out tomography through the thickness of the structure 1. In particular, the structure 1 being a multilayer structure, the modelled structure can be sliced up into as many layers as the structural element 1, so as to qualify each layer. Nevertheless, there is not necessarily any link between the layering of the structural element 1 and that of the model.

Figure 13:
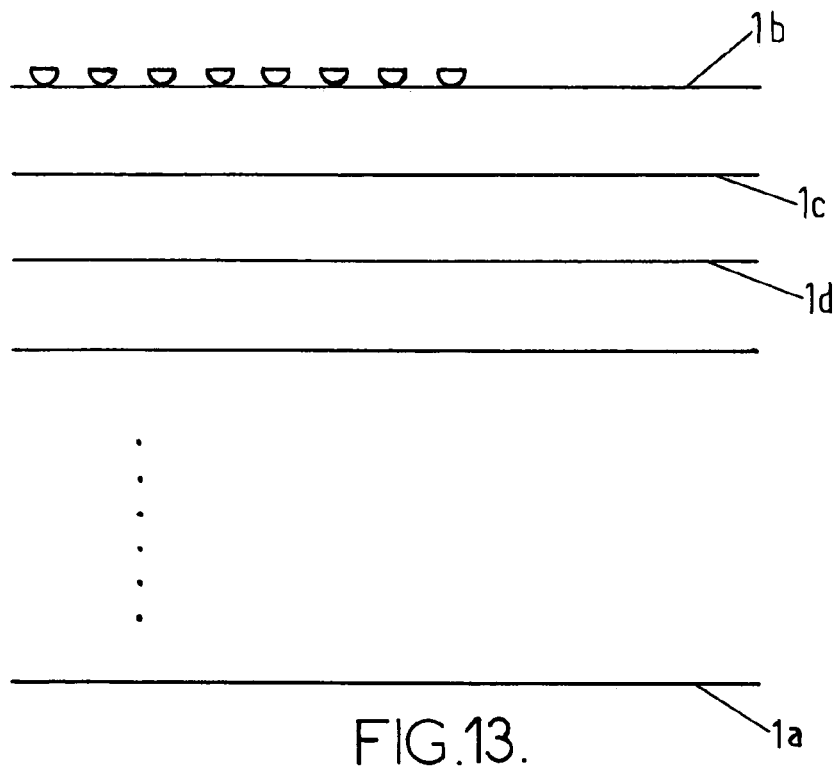
FIG. 13 is a diagrammatic side view representative of the calculation corresponding to a multilayer structure.

Reference is made to FIG. 13 for the analysis of this embodiment.

Initially, the structure is excited by a current at a high frequency suitable for loading the structure chiefly at the surface. A frequency is for example chosen such that the attenuation of the field in the structure between the internal face 1*b* and the other face 1*c* of the modelled surface layer is sufficient for it to be possible to neglect the influence of the layers situated under the surface layer (for example an attenuation about equal to 10).

The steps of I/ or of II/ are performed for the surface layer alone. By way of example, the surface a of FIG. 6*a* is then the face 1*c* of the structural element 1. The values of conductivity σ and permittivity $\epsilon_r$ are thus obtained at the level of the surface layer.

Next, the structure is excited at a lower frequency, so that the attenuation by a factor of for example 10 is for example obtained between the face 1*b* and a yet deeper face 1*d* of the structure. By repeating the calculation of I/ or of II/ for that part of the structural element lying between the faces 1*b* and 1*d*, information is obtained about the values of conductivity σ and permittivity $\delta_r$ for these two layers aggregated. With the aid of the previous calculation of the conductivity σ and permittivity $\epsilon_r$ values in the surface layer, these values are deduced for just the intermediate layer lying between the faces 1*c* and 1*d*.

One continues thus, lowering the frequency successively, to obtain for each new layer, the sought-after conductivity σ and permittivity $\epsilon_r$ values.

Of course, one might wish to search for only one of these values, and it would, for this purpose, be possible to measure and calculate only one of the two components $E_X$ or $E_Y$, and deduce therefrom only one component $\epsilon_r$ or σ by applying the left branch or the right branch of the algorithm of FIG. 12.

Alternatively, it would be possible to begin with a low frequency to obtain an overall picture of the structure, then to gradually increase the frequency to obtain information about the successive layers closer and closer to the emission layer 4.

Other variants are possible, such as for example scanning the structure firstly by increasing the frequency in successive steps and then by reducing it down to its initial value, or other variants.

According to one variant, the device for integrated monitoring of structures is not necessarily fixed on an internal 1*b* or external 1*a* face, but may be inserted into the structure, in which case the previous calculations will have to be carried out by summing the results provided for the two portions of structure separated by the device, each exhibiting a reflection matrix and a transmission matrix.

Thus the central unit 3 is on the one hand suitable for controlling the excitation of the conducting tracks 9 of the emission layer 4, of the conducting tracks 12 of the detection layer 5, the switching of the breakers 11, and the processing of the signal detected, and on the other hand comprises calculation means comprising memory means that can contain a model of the structure under study, means for estimating the components $E_X$ and $E_Y$, means of comparing these values with the measurements, means of generating a modified model. Finally, the central unit can comprise a database of earlier results for the structure under test or of the results obtained for one or more similar structures. Certain of these elements may furthermore be placed on an information support such as a CD-ROM, a DVD-ROM, or other, able to be read by a computer.

The information provided by the method and the device according to the invention could also be used jointly with that provided by the SMART-layer device for integrated monitoring of structures from the company Acellent based on piezoelectric sensor technology, whose ability to detect defects of a mechanical origin is recognized.

Figure 14:
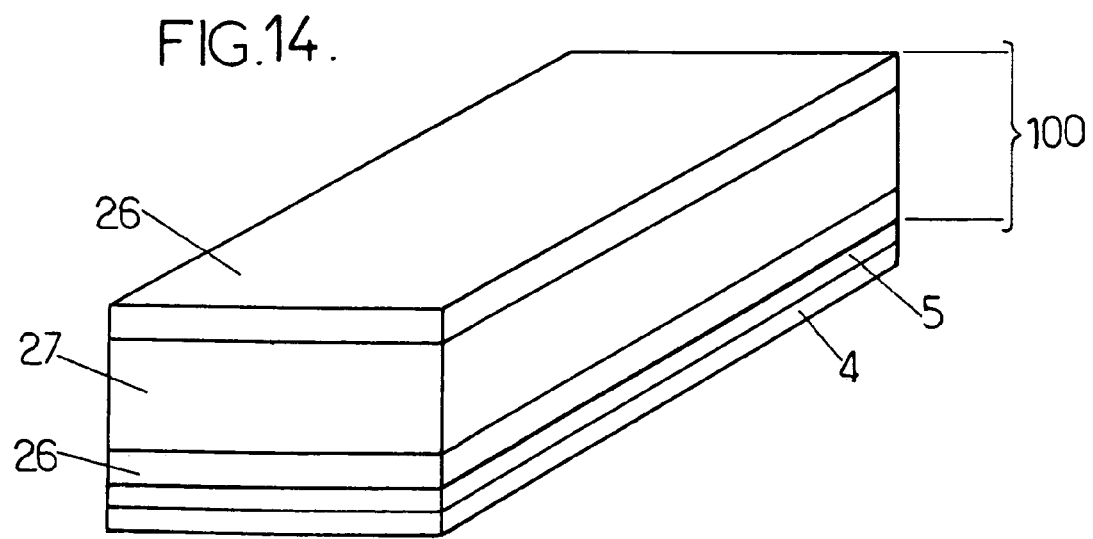
FIG. 14 is a perspective view representing another type of structure, of the sandwich kind, that may be furnished with a device according to a second embodiment of the invention.

The method and the device described here are not confined exclusively to use for composite structures comprising on the one hand a matrix consisting of a dielectric material and, on the other hand, of carbon fibres exhibiting electrical conductivity. It is for example possible to use the device and the method according to the invention for a sandwich structure, such as represented in FIG. 14, which is purely dielectric. In this case, there is of course no question of determining any electrical conductivity σ for the carbon fibres, but the device according to the invention can be used to determine the dielectric permittivity $\epsilon_r$ of the structural element 1. The latter can for example consist of one or more layers 26 of resin reinforced with glass fibres, and of a core 27 disposed between these layers. In this case, the device for integrated monitoring of structures no longer operates according to a hybrid technology, but according to a purely electrical method, in which the emission layer 4 is modified to generate an electric field E rather than a magnetic field. This is carried out very simply by opening the switches 11 (FIG. 4) previously linking the conducting tracks 9*a* and 9*b*, so as to generate an electric field in each of the conducting tracks 9*a*, 9*b*, etc. successively.

The solution algorithm of FIGS. 8 and 9 is now used only to determine the value $\epsilon_r$ of the dielectric permittivity of the instrumented structure. Under these conditions, it is now possible not to measure the component $E_X$ of the electric field detected, and we can make do with a detection layer oriented along the direction Y, such as that represented at 5*a* in FIG. 5*a*.

Of course, the emission and detection layers 4, 5, may be situated on the internal face 1*b* of the sandwich structural element 1, or on its external face, or be split so as to be placed respectively at various levels in the thickness of the structural element 1.

The invention claimed is:

1. Device for health monitoring of an area of a structural element comprising at least one dielectric material of dielectric permittivity $\epsilon_r$, comprising:
    (A) means of emission of electromagnetic radiation extending in a direction, the electromagnetic field generating an electric field in the area,
    (B) detection means suitable for measuring a first measured component of an electric field, along a first direction of detection, and
    (C) calculation means suitable for obtaining a value of the dielectric permittivity $\epsilon_r$ in the area on the basis of the first measured component, in which the structural element is an inhomogeneous structural element comprising an imperfectly conducting material, of electrical conductivity σ, in which the means of emission is means of emission of magnetic radiation that is suitable for generating a magnetic field, the magnetic field being, at the area, equivalent to a magnetic field emitted by a magnetic dipole extending in the direction, and in which the calculation means is furthermore suitable for obtaining a value of the electrical conductivity σ in the area on the basis of the first measured component.

2. Device according to claim 1, in which the detection means is suitable for furthermore measuring a second measured component of the electric field, along a second direction of detection forming with the first direction of detection a nonzero angle, and in which, the calculation means is suitable for obtaining a value of the electrical conductivity σ and of the electrical permittivity $\epsilon_r$ in the area on the basis of the first and the second measured components.

3. Device according to claim 2, in which a direction chosen from the first and the second direction of detection is the direction of means of emission.

4. Device according to claim 1, in which the means of emission comprises a layer comprising, at the area, at least two parallel conducting tracks, oriented along the dipole direction and suitable for being able to be traversed in mutually opposite senses by an electric current.

5. Device according to claim 2, in which the detection means comprises a layer comprising, at the area, at least one conducting track oriented along the first direction of detection, and a layer comprising, at the area, at least one conducting track oriented along the second direction of detection.

6. Device according to claim 1, in which the calculation means comprises:
(Z) memory means suitable for containing a model of the area by at least two numerical parameters related to $\sigma^s$ representing the electrical conductivity σ in this area, and $\epsilon_r^s$ representing the dielectric permittivity in this area, and a model of the means of emission,
(E) estimation means suitable for estimating a simulated component of a simulated electric field generated in the model of the area by the model of means of emission, along the first direction of detection, and
(F) comparison means suitable for comparing the simulated component and the corresponding measured component obtained by the means of detection (B).

7. Device according to claim 2, in which the calculation means comprises:
(Z) memory means suitable for containing a model of the area by at least two numerical parameters related to $\sigma^s$ representing the electrical conductivity σ in this area, and $\epsilon_r^s$ representing the dielectric permittivity in this area, and a model of the means of emission,
(E) estimation means suitable for estimating a first and a second simulated component of the simulated electric field along the first and second directions of detection, and
(F) comparison means suitable for comparing the simulated components and the corresponding measured components obtained by the detection means (B).

8. Device according to claim 6 furthermore comprising (D) generating means suitable for generating the model contained in the memory means (Z).

9. Device according to claim 1, furthermore comprising
(G) a database containing data relating to an energy absorbed by a structural element exhibiting an electrical conductivity σ and a dielectric permittivity $\epsilon_r$ for the materials.

10. Device according to claim 1, furthermore comprising a layer for integrated monitoring of the structures based on piezoelectric technology.

11. Device according to claim 1 in which the structural element comprises no imperfectly conducting material,
and in which the means of emission is means of emission of electrical radiation that is suitable for generating an electric field extending in the direction.

12. Structure suitable for health monitoring of an area of a structural element of the structure, and comprising:
at least one dielectric material of dielectric permittivity $\epsilon_r$,
an electromagnetic radiation emission layer extending in a direction, the electromagnetic field generating an electric field in the area,
a detection layer suitable for measuring a first measured component of an electric field, along a first direction of detection, and
at least one facility for connection to a calculation means suitable for obtaining a value of the dielectric permittivity $\epsilon_r$ in the area on the basis of the first measured component, in which the structural element is an inhomogeneous structural element comprising an imperfectly conducting material, of electrical conductivity σ, in which the means of emission comprises means of emission of magnetic radiation that is suitable for generating a magnetic field, the magnetic field being, at the area, equivalent to a magnetic field emitted by a magnetic dipole extending in the direction, and in which the calculation means is alternatively suitable for obtaining a value of the electrical conductivity σ in the area on the basis of the first measured component.

13. Structure according to claim 12, the structural element taking the form of at least one layer, the detection layer being disposed between the structural element layer and the emission layer.

14. Structure according to claim 12, the structural element taking the form of at least one layer, the emission layer being disposed between the structural element layer and the detection layer.

15. Structure according to claim 12, the structural element taking the form of at least one layer, the structural element layer being disposed between the emission layer and the detection layer.

16. Structure according to claim 12, the inhomogeneous structural element taking the form of at least one fine layer comprising at least one imperfectly conducting material in the form of at least one carbon fibre, of electrical conductivity σ, and one dielectric material in the form of a matrix of dielectric permittivity $\epsilon_r$, in which the carbon fibres are embedded.

17. Method for health monitoring of an area of a structural element comprising at least one dielectric material of dielectric permittivity $\epsilon_r$, the method comprising:
(a) generating an electromagnetic field by means of emission of electromagnetic radiation extending in a direction, the electromagnetic field generating an electric field in the area,
(b) generating a magnetic field by means of emission of magnetic radiation while generating the electromagnetic field, the magnetic field being, at the area, equivalent to a magnetic field emitted by a magnetic dipole extending in the direction;
(c) measuring a first measured component of an electric field along a first direction of detection by means of detection means, and
(d) obtaining at least one of a value of the dielectric permittivity $\epsilon_r$ in the area or a value of the electrical conductivity σ in the area on the basis of the first measured component by means of calculation means, in which the structural element is an inhomogeneous structural element comprising an imperfectly conducting material, of electrical conductivity σ.

18. Method according to claim 17, in which, during first iteration, steps (a) to (c) are performed for a first frequency of the emission means,
during a second iteration, steps (a), (b) and (c) are repeated for a second frequency, and
during step (c) of the second iteration, the value obtained during step (c) of a previous iteration is taken into account.

19. Method according to claim 17, in which, during each step (b), a second measured component of the electric field is furthermore measured, along a second direction of detection forming with the first direction a nonzero angle, and in which, during step (c) of each iteration, the first and second measured components are taken into account.

20. Method according to claim 17, in which, during step (c), for each iteration, furnished, in memory means, with an initial model of the area by at least two numerical parameters related to $\sigma^s$ representing the electrical conductivity $\sigma$ in this area, and $\epsilon_r^s$ representing the dielectric permittivity in this area, and a model of the emission means, (e) at least one first simulated component of a simulated electric field generated in the model of the area by the model of means of emission is estimated, along a direction of detection chosen from the first and second direction of detection, and (f) the simulated component and the corresponding measured component obtained during step (b) are compared.

21. Method according to claim 20, furthermore comprising, prior to step (e), a step (d) in which an initial model of the area by at least two numerical parameters related to $\sigma^s$ representing the electrical conductivity $\sigma$ in this area, and $\epsilon_r^s$ representing the dielectric permittivity in this area, and a model of the means of emission, are generated in the memory means.

22. Method according to claim 20, in which, during step (b), a second measured component of the electric field is measured, along the other direction of detection, in which, during step (e), a second corresponding simulated component of the simulated electric field is estimated, and in which, during step (f), the second simulated component and the second measured component obtained during step (b) are compared.

23. Method according to claim 20, in which, subsequent to step (f), step (d') is furthermore implemented, in which a modified model of the area is generated by at least two numerical parameters related to $\sigma^s$ representing the electrical conductivity $\sigma$ in this area, and $\epsilon_r^s$ representing the dielectric permittivity in this area, differing from the initial model through at least one of the numerical parameters, and steps (e) and (f) are implemented for the modified model.

24. Method according to claim 20, in which step (c) furthermore comprises a step (g) during which at least one characteristic of the area chosen from the conductivity $\sigma$ and the permittivity $\epsilon^r$ is determined by identifying the simulated conductivity $\sigma^s$ with the conductivity and/or the simulated permittivity $\epsilon_r^s$ with the permittivity, as soon as the comparison performed in step (f) gives a satisfactory result.

25. Method according to claim 17, furthermore comprising a step during which (h) an energy absorbed by the structural element exhibiting the electrical conductivity $\sigma$ and/or the dielectric permittivity $\epsilon_r$ that are obtained in step (c) is determined by inference on a database containing data pertaining to an energy absorbed by a structural element exhibiting an electrical conductivity $\sigma$ and a dielectric permittivity $\epsilon_r$, for the materials.

26. Method according to claim 17 in which the structural element comprises no, even imperfectly, electrically conducting material, in which, during step (a), an electric field is generated in the area, in the direction, with the aid of means of emission of electrical radiation.

27. Method according to claim 26, in which, during step (c), furnished, in memory means (3), with an initial model of the area by at least one numerical parameter related to $\epsilon_r^s$ representing the dielectric permittivity in this area, and a model of the means of emission, (d) a simulated component of a simulated electric field induced in the model of the area by the model of means of emission is estimated, and (e) the simulated component and the corresponding measured component obtained during step (b) are compared.

* * * * *

UNITED STATES PATENT AND TRADEMARK OFFICE
CERTIFICATE OF CORRECTION

| | |
|---|---|
| PATENT NO. | : 7,460,963 B2 |
| APPLICATION NO. | : 10/813466 |
| DATED | : December 2, 2008 |
| INVENTOR(S) | : Michel B. Lemistre et al. |

It is certified that error appears in the above-identified patent and that said Letters Patent is hereby corrected as shown below:

At Column 24, line 9, "$\varepsilon^r$" should be -- $\varepsilon_r$ --.

Signed and Sealed this

Eighth Day of September, 2009

David J. Kappos
*Director of the United States Patent and Trademark Office*